US006379652B1

(12) United States Patent
Liu et al.

(10) Patent No.: US 6,379,652 B1
(45) Date of Patent: Apr. 30, 2002

(54) ORAL COMPOSITIONS FOR REDUCING MOUTH ODORS

(75) Inventors: Xiaoyan Liu, Highland Park; Malcolm Williams, Piscataway; Ravi Subramanyam, Belle Mead; John Hughes, Cranbury, all of NJ (US)

(73) Assignee: Colgate Palmolive Company, New York, NY (US)

( * ) Notice: Subject to any disclaimer, the term of this patent is extended or adjusted under 35 U.S.C. 154(b) by 0 days.

(21) Appl. No.: 09/688,660

(22) Filed: Oct. 16, 2000

(51) Int. Cl.[7] .............................. A61K 7/16; A61K 7/26
(52) U.S. Cl. ............................................ 424/49; 424/58
(58) Field of Search ...................... 424/49–58

(56) References Cited

U.S. PATENT DOCUMENTS

| 4,844,883 A | * | 7/1989 | Patel ............................ 424/49 |
| 4,923,685 A | * | 5/1990 | Wuelknitz et al. ............. 424/54 |
| 5,298,238 A | * | 3/1994 | Hussein et al. ................ 424/49 |
| 5,330,771 A | * | 7/1994 | Barkalow et al. ............... 426/3 |
| 5,372,824 A | * | 12/1994 | Record et al. .................. 426/3 |
| 5,554,588 A | * | 9/1996 | Behan et al. .................. 512/1 |
| 5,559,271 A | * | 9/1996 | Shaw et al. .................... 568/21 |
| 5,628,986 A | * | 5/1997 | Sanker et al. ................. 424/49 |
| 5,725,865 A | * | 3/1998 | Mane et al. .................. 424/401 |
| 5,733,530 A | * | 3/1998 | Balla et al. .................... 424/52 |
| 5,843,466 A | * | 12/1998 | Mane et al. ................. 424/401 |
| 6,042,812 A | * | 3/2000 | Sanker et al. ................. 424/49 |
| 6,121,315 A | * | 9/2000 | Nair et al. ..................... 424/49 |

OTHER PUBLICATIONS

CAPLUS 1999:733316 CA132:93482, CODEN:FFJOED, Abstracts of Griffin et al Flavour Fragrance J. 14(5):322–332 "The Role of Structure and Molecular Properties of Terpenoids in Determining Their Antimicrobial Activity" ISSN:0882–5734, 1999.*

* cited by examiner

Primary Examiner—Shep K. Rose
(74) Attorney, Agent, or Firm—Paul Shapiro

(57) ABSTRACT

A method to suppress oral malodor and provide long lasting breath protection wherein there is applied to the oral cavity of the user an oral composition comprising an orally acceptable vehicle containing therein a flavor system comprised of a mixture of an essential oil and a coolant compound which is a menthyl ester of naturally occurring hydrocarboxylic acids having 2 to 6 carbon atoms esterified with $C_1$–$C_4$ alkyl groups.

11 Claims, No Drawings

ORAL COMPOSITIONS FOR REDUCING MOUTH ODORS

BACKGROUND OF THE INVENTION

1. Field of the Invention

The present invention relates to an oral composition useful for reducing oral malodor.

2. The Prior Art

"Oral composition" means a composition for topical applications to the oral cavity to clean and care for the teeth as well as the oral cavity surfaces. Representative of such compositions are oral hygiene products for delivering therapeutic and cosmetic benefits to the oral cavity such as mouthwashes or rinses, toothpaste, dental gels, tooth powder, chewing gum, lozenges, strips and similar products. The benefits delivered by oral compositions include the suppression of dental calculus formation and the prevention of dental disorders such as caries, periodontitis and gingivitis as well as the elimination of halitosis.

Dental plaque is a deposit which forms on teeth and consists of inorganic and organic components derived from saliva, food and bacteria which are present in the oral cavity. When plaque undergoes calcification it forms dental calculus composed largely of calcium and orthophosphate arranged in a crystal lattice called hydroxyapatite.

Oral malodor, or halitosis, is caused by the putrefactive activity of microorganisms on appropriate substrate components of dental plaque, debris adhering to mucous membranes and salivary cellular elements to produce volatile sulfur compounds primarily hydrogen sulfide, methyl mercaptan and traces of methyl sulfide.

Methods of inhibiting volatile sulfur compounds to reduce the production of mouth odor have included the use of oral compositions such as toothpastes and mouthrinses containing antibacterial agents, such as, chlorhexidine. However, the side effects associated with chlorhexidine, such as a bitter taste and staining of the teeth, tongue, gums and oral mucosa, precludes the use of chlorhexidine in oral compositions.

Essential oils used as flavoring and taste masking agents in oral compositions are also known to the art to have antibacterial activity. Essential oils are aromatic compounds that are either derived from plant sources or are synthesized. Some essential oils show long lasting antiseptic effectiveness against the most common pathogens in the mouth most frequently associated with oral malodor, plaque, and gingivitis.

Essential oils have been used for years in antiseptic and antiplaque toothpastes. For example, U.S. Pat. No. 5,094,843 teaches an antiplaque toothpaste with a fluorine source, and a specific range of the essential oils thymol, menthol, methyl salicylate and eucalyptol.

U.S. Pat. No. 5,356,615 teaches an antiplaque oral composition, including a toothpaste containing the antibacterial agent Triclosan. The antiplaque activity of the Triclosan is increased by essential oils such as eucalyptol, thymol, methyl salicylate and menthol.

While the prior art discloses toothpaste and other oral compositions containing antiseptic essential oils, there is a continuing search by the art to improve and enhance the antiseptic efficacy of oral compositions prepared with these oils and particularly with the suppression of oral malodor.

SUMMARY OF THE INVENTION

In accordance with the present invention there is provided a method to suppress oral malodor to provide long lasting breath protection wherein there is applied to the oral cavity of the user an oral composition comprising an orally acceptable vehicle containing therein a flavor system comprised of a mixture of essential oils and a coolant compound, which is a menthol ester of naturally occurring hydrocarboxylic acids having 2 to 6 carbon atoms esterified with $C_1$–$C_4$ alkyl groups.

DETAILED DESCRIPTION OF THE INVENTION

The term "coolant compound" as used herein means a compound which provides a cooling sensation when ingested or contacted with the body. These compounds are well known to the art. For example, German patent application 2608226 discloses compounds which exhibit a physiological cooling effect. The cooling compounds disclosed therein include menthol esters of naturally occurring hydroxycarboxylic acids having 2 to 6 carbon atoms which are esterified with $C_1$–$C_4$ alkyl groups and include such menthyl esters such as menthyl acetate and menthyl lactate. It is these very same compounds when combined with essential oils having antibacterial properties have unexpectedly been discovered to substantially enhance the antibacterial efficacy of essential oil flavor systems and particularly with respect to the suppression of oral malodor.

A flavor system of the present invention which exhibits enhanced antibacterial activity concomitant with suppression of oral malodor is generally comprised of about 1 to about 50% by weight of the coolant compound preferably about 5.0 to about 30% by weight of the coolant compound and about 50 to about 99% by weight and more preferably 70 to about 95% by weight of one or more of antiseptic essential oil flavors such as thymol, eugenol, eucalyptus and tea tree oil, oil of wintergreen, oil of pepper mint, oil of spearmint, clove bud oil, menthol, anethole, methyl salicylate, cassia, sage, parsley oil, oxanone, alpha-irisone, marjoram, lemon, orange, propenyl guaethol, cinnamon, vanillin, ethyl vanillin, heliotropine, 4-cis-heptenal, diacetyl, methyl-para-tert-butyl phenyl acetate, and mixtures thereof.

The flavor system of the present invention is effective to impart odor suppression to oral care compositions when present in the oral care composition at concentrations of from about 0.5 to about 10.0 by weight and preferably at about 1 to about 2% by weight.

To further enhance the activity of the flavor system of the present invention, an antibacterial enhancing agent may be included in the oral composition. The use of such antibacterial enhancing agents in oral care compositions is known to the art, as for example, U.S. Pat. Nos. 5,188,821 and 5,192,531.

Antibacterial enhancing agents preferred for use in the practice of the present invention include a natural or synthetic anionic polycarboxylates having a molecular weight of about 1,000 to about 5,000,000, preferably about 30,000 to about 500,000. Synthetic anionic polycarboxylates are generally employed in the form of their free acids or preferably partially or more preferably fully neutralized water soluble alkali metal (e.g. potassium and preferably sodium) or ammonium salts. Preferred are 1:4 to 4:1 copolymers of maleic anhydride or acid with another polymerizable ethylenically unsaturated monomer, preferably methyl vinyl either/maleic anhydride having a molecular weight (M.W.) of about 30,000 to about 1,000,000, most preferably about 30,000 to about 500,000. These copolymers are available, for example, under the trade designation Gantrez AN 139 (M.W. 500,000), AN 119 (M.W. 250,000); and preferably Gantrez S-97 Pharmaceutical Grade (M.W. 70,000), of GAF Corporation.

Other anionic polycarboxylates useful in the practice of the present invention include the 1:1 copolymers of maleic anhydride with ethyl acrylate, hydroxyethyl methacrylate, N-vinyl-2-pyrollidone, or ethylene, the latter being available, for example, as Monsanto EMA No: 1103, M.W. 10,000 and Grade 61, and 1:1 copolymers of acrylic acid with methyl or hydroxyethyl methacrylate, methyl or ethyl acrylate, isobutyl methacrylate, isobutyl vinyl ether or N-vinyl-2-pyrrolidone.

Additional operative useful polycarboxylate compounds include copolymers of maleic anhydride with styrene, isobutylene or ethyl vinyl either, polyacrylic, polycationic and polymaleic acids, and sulfonacrylic oligomers of M.W. as low as 1,000 available under the trade designation Uniroyal ND-2.

Also useful in the practice of the present invention are the so-called carboxyvinyl polymers, commercially available, for example, under the trade designation Carbopol 934, 940 and 941 from B.F. Goodrich, these polymers consisting of a colloidally water-soluble polymer of polyacrylic acid crosslinked with from about 0.75% to about 2.0% of polyalkyl sucrose or polyalkyl pentaerythritol as a cross linking agent, often with M.W.'s up to 4–5 million or more.

The antibacterial enhancing agent, when employed in the oral composition, is incorporated in the compositions in weight amounts of about 0.05 to about 5%, preferably about 0.1 to about 3%.

Fluoride ions may also be included in the oral compositions of the present invention to provide an anticaries effect. Among these materials are inorganic fluoride salts, such as soluble alkali metal fluoride salts, for example, sodium fluoride, potassium fluoride, sodium monofluorophosphate and sodium hexafluorosilicate. Alkali metal and tin fluorides, such as sodium and stannous fluorides, sodium monofluorophosphate and mixtures thereof, are preferred.

The amount of fluorine-providing salt is generally present in the oral composition at a concentration of about 0.0005 to about 3.0% by weight. Any suitable minimum amount of such salt may be used, but it is preferable to employ sufficient fluoride salt to release about 300 to 2,000 ppm, more preferably about 800 to about 1,500 ppm, of fluoride ion.

The oral composition of the present invention may be a solution of ingredients such as a mouthrinse or it maybe a semi-solid such as a toothpaste or gel dentifrice or chewing gum or solid lozenge.

In the aspect of this invention wherein the oral composition is a gel or paste, an orally acceptable vehicle, including a water-phase with humectant which is preferably glycerine or sorbitol or an alkylene glycol such as polyethylene glycol or propylene glycol is present, wherein water is present typically in an amount of about 15–40% by weight and glycerine, sorbitol and/or the alkylene glycol (preferably propylene glycol) typically total about 20–75% by weight of the oral composition, more typically about 25–60% by weight.

When the oral composition is substantially semi-solid or pasty in character, such as a toothpaste or gel, the dentifrice vehicle may contain a dentally acceptable abrasive material such as sodium bicarbonate or water insoluble abrasive material such as sodium metaphosphate, potassium metaphosphate, tricalcium phosphate, dihydrated dicalcium phosphate, anhydrous dicalcium phosphate, calcium pyrophosphate, calcium carbonate, aluminum silicate, hydrated alumina, calcined alumina, silica, bentonite, and mixtures thereof.

The abrasive material is generally present in the paste or gel composition in weight concentrations of about 10% to about 60% by weight, preferably about 10% to about 30% in a gel and about 25% to about 60% in a paste.

Toothpastes as well as gel dentifrices typically contain a natural or synthetic thickener or gelling agent in proportions of about 0.1 to about 10% by weight, preferably about 0.5 to about 5% by weight. Suitable thickeners or gelling agents include Irish moss, iota-carrageenan, kappa-carrageenan, gum tragacanth, starch, polyvinylpyrrolidone, hydroxyethyl propyl cellulose, hydroxybutyl methyl cellulose, hydroxypropyl methyl cellulose, hydroxyethyl cellulose and sodium carboxymethyl cellulose.

In the aspect of the present invention wherein the oral composition is substantially liquid in character such as a mouthwash or rinse, the vehicle is typically a water-alcohol mixture. Generally, the weight ratio of water to alcohol is in the range of from about 3:1 to 10:1 and preferably about 4:1 to about 6:1. The alcohol is a non-toxic alcohol such as ethanol or isopropanol. A humectant such as glycerine, sorbitol or an alkylene glycol such as polyethylene glycol or preferably propylene glycol may be present in amount of about 10–30% by weight. Mouthrinses typically contain about 50–85% of water, about 0 to 20% by weight of a non-toxic alcohol and about 10–40% by weight of the humectant.

Surfactants are used in the compositions of the present invention to achieve increased prophylactic action and assist in achieving thorough and complete dispersion of the flavor. The surfactant material is preferably anionic, suitable examples which include water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkyl sulfoacetates, higher fatty acid esters of 1,2- dihydroxy propane sulfonate, and the substantially saturated higher aliphatic acyl amides of lower aliphatic amino carboxylic acid compounds, such as those having 12 to 16 carbons in the fatty acid, alkyl or acyl radicals and alkoyl taurines, and the like. Examples of the last mentioned amides and taurates are N-lauroyl sarcosine, and the sodium, potassium and ethanolamine salts of N-lauroyl, N-myristoyl, or N-palmitoyl sarcosine which should be substantially free from soap or similar higher fatty acid material as well as N-methyl-N-cocoyl (or oleoyl or palmitoyl) taurines.

Any suitable sweetening material may also be employed. Examples of suitable sweetening agents include sucrose, lactose, maltose, xylitol, sodium cyclamate, perillartine, aspartyl phenyl alanine methyl ester, saccharine and the like. Suitably, sweetening agents may each or together comprise from about 0.1% to 5% of the oral composition.

Antitartar agents such as sodium tripolyphosphate, tetrapotassium or tetrasodium pyrophosphate, or mixtures thereof, can be present in the oral compositions of the present invention at concentrations from about 0.5 to about 8% by weight.

Agents used to diminish teeth sensitivity such as potassium chloride, potassium nitrate and potassium citrate can also be included in oral compositions of the present invention at concentrations of about 0.1 to about 10% by weight.

Various other materials may be incorporated in oral compositions of this invention including preservatives, such as sodium benzoate, vitamins and chlorophyll compounds. These adjuvants, when present, are incorporated in the compositions in amounts which do not substantially adversely affect the properties and characteristics desired.

The oral compositions of the present invention may be prepared by suitably mixing the ingredients. For instance, in the preparation of a mouthrinse, flavor system combination is dispersed in a mixture of ingredients, e.g. alcohol, humectants, surfactants, and flavor are then added and mixed. The ingredients are then mixed under vacuum for about 15–30 minutes. The resulting rinse product is then packaged. Dentifrices are prepared similarly, additional thickener and polishing agents being included in the last or penultimate step.

The following Examples further illustrate the present invention, but it is understood that the invention is not limited thereto. All amounts and proportions referred to herein and in the appended claims are by weight unless otherwise indicated.

EXAMPLE I

A 1% by weight solution in ethanol of a series of individual essential oil flavors were prepared and evaluated in an MIC assay for bactericidal activity against F. nucleatum. The bacterial strain F. nucleatum is implicated in the occurrence of oral malodor.

MIC ASSAY

The bacterial strains of F. nucleatum were grown for 24 hours in thioglycolate broth for 48 hours at 37° C. The optical density at 610 nM was adjusted to between 0.1 to 0.2 prior the MIC determination.

MIC determinations were performed using the microtiter format according to standard procedures (Manual of clinical Microbiology, 1995). The results are recorded in Table I below. The lower the MIC value, the more effective is the antibacterial efficacy of the flavor components.

TABLE I

| Flavors | MIC Value |
| --- | --- |
| Cinnamic aldehyde | 125 |
| Menthyl ester* | 125 |
| Thymol | 125 |
| Eugenol | 250 |
| Tea tree oil | 250 |
| Spearmint | 375 |
| Eucalyptus | 375 |
| Cornmint oil | 375 |
| Eucalyptol | 500 |
| Anethol | 500 |
| Peppermint | 500 |
| L-menthol | 500 |

*The methyl ester was a mixture of menthyl acetate and menthyl lactate.

The results recorded in Table I show that the mixture of the menthyl ester and essential oil flavors, tea tree oil, eugenol, cinnamic aldehyde and thymol exhibit good bactericidal activity against F. nucleatum.

EXAMPLE II

The procedure of Example 1 was repeated except combinations of various flavor compounds were evaluated for antibacterial efficacy via the MIC assay. The results are recorded in Table II below.

TABLE II

| Composition No. Flavor Combinations | MIC Value |
| --- | --- |
| 1. Menthyl ester* + tea tree oil | 31.3 |
| 2. Menthyl ester + thymol | 31.3 |
| 3. Menthyl ester + eugenol | 62.5 |
| 4. Menthyl ester + eucalyptus | 62.5 |
| 5. Menthyl ester + spearmint | 62.5 |
| 6. Eugenol + thymol | 125.0 |
| 7. Eucalyptus + thymol | 125.0 |
| 8. Spearmint + eugenol | 125.0 |
| 9. Spearmint + thymol | 125.0 |

*The menthyl ester was a mixture of menthyl acetate and menthyl lactate.

The MIC results recorded in Table II indicate that unexpectedly combinations of the menthyl ester coolant mixture with a second flavor component unexpectedly exhibited MIC values 2 to 4 times lower than flavor combinations in which the menthyl ester was absent, thereby demonstrated the improved antibacterial activity occasioned by the presence of the menthyl ester in the combination.

EXAMPLE III

A flavor system having the ingredients listed in Table III was prepared and incorporated in a dentifrice composition designated "Composition A" containing the ingredients listed in Table IV below.

TABLE III

| Components | Flavor System (wt. %)* |
| --- | --- |
| Anethole | 13 |
| Cornmint oil | 19 |
| Menthol | 25 |
| Eucalyptus oil | 2 |
| Spearmint oil | 5 |
| Peppermint | 11 |
| Menthyl lactate | 19 |
| Thymol | 6 |
| Total | 100 |

For purposes of comparison, a dentifrice having substantially same ingredients as Composition A except a flavor mixture of anethol, cinnamic acid euganol, menthol and peppermint was used so that the dentifrice designated "Composition B" functioned as a placebo.

TABLE IV

| Components | Weight % |
| --- | --- |
| Deionized water | 14.076 |
| Glycerin | 15.00 |
| Carrageenan | 0.400 |
| Sodium saccharin | 0.300 |
| Sodium fluoride | 0.320 |
| Noncrystalizing sorbitol (70%) | 42.42 |
| Gantrez S-97 | 0.500 |
| Silica abrasive | 23.5 |
| Flavor system | 1.20 |
| Sodium hydroxide - 50% solution | 0.500 |
| Dye | 0.034 |
| Sodium lauryl sulfate | 1.7500 |
| Total | 100.000 |

A human study was conducted to compare the 4 hour effect of Composition A on the volatile sulfur compounds (VSC) responsible for mouth odor. VSC levels were measured using a gas chromatograph equipped with a flame photometric detector, using a breath sample extracted from the subject's mouth directly into the sample port of the detector. A VSC level above 10 nanograms (ng)/ml is considered to result in offensive mouth odor.

Fifteen subjects were involved in a randomized, double blind study design with a cross over phase. After an initial morning baseline evaluation, and breakfast, subjects brushed with their assigned dentifrice composition for 1 minute. After the subjects used the assigned dentifrice, they were asked to return to the study site 4 hours later for post treatment evaluation. After a 1 day washout period between each treatment product, the subjects repeated the same treatment procedure with a newly assigned product during the cross over phase. Each subject used each of the 2 compositions A and B. During the washout period, subjects used a regular commercial fluoride dentifrice.

The VSC levels observed in the study are recorded in Table IV below.

TABLE IV

VSC (NG/ML)

| Composition | Baseline (N) | Mean Baseline Use (ng/ml) | Final* Mean |
|---|---|---|---|
| A | 15 | 16.38 | 9.87 |
| C | 15 | 15.39 | 11.15 |

The results recorded in Table IV indicate that Composition A, as well as the placebo Composition B, significantly reduced VSC levels for 4 hours when compared to baseline values. However, Composition A reduced VSC formation below the offensive level.

What is claimed is:

1. A method to suppress oral malodor and provide long lasting breath protection in the oral cavity comprising applying to the oral cavity an oral composition comprising an orally acceptable vehicle containing therein a flavor system comprised of a mixture of an essential oil and a coolant compound which is a menthyl ester of a hydrocarboxylic acid having 2 to 6 carbon atoms esterified with $C_1$–$C_4$ alkyl groups, the essential oil having bactericidal activity against bacteria implicated in the occurrence of oral malodor, the presence of the menthyl ester substantially enhancing the antibacterial efficacy of the essential oil in the suppression of oral malodor to a non-offensive level.

2. The method of claim 1 wherein the menthyl ester is menthyl lactate.

3. The method of claim 1 wherein the menthyl ester is menthyl acetate.

4. The method of claim 1 wherein the menthyl ester is a mixture of menthyl acetate and menthyl lactate.

5. The method of claim 1 wherein the flavor system is comprised of about 1 to about 50% by weight of the coolant compound and about 50 to about 99% by weight of an essential oil.

6. The method of claim 1 wherein the flavor system is comprised of about 5 to about 30% by weight of the coolant compound and about 70 to about 95% by weight of the essential oil.

7. The method of claim 1 wherein the essential oil is tea tree oil.

8. The method of claim 1 wherein the essential oil is thymol.

9. The method of claim 1 wherein the essential oil is eugenol.

10. The method of claim 1 wherein the essential oil is eucalyptus oil.

11. The method of claim 1 wherein the essential oil is spearmint oil.

* * * * *